(12) United States Patent
Kay et al.

(10) Patent No.: US 7,325,470 B2
(45) Date of Patent: Feb. 5, 2008

(54) SELF-CENTERING SCREW AND RETAINING SCREW DRIVER FOR USE IN SURGERY

(75) Inventors: David B. Kay, Akron, OH (US); Lee A. Stmad, Broadview Hts., OH (US); Dustin Ducharme, Akron, OH (US)

(73) Assignee: Orthohelix Surgical Designs, Inc., Akron, OH (US)

( * ) Notice: Subject to any disclaimer, the term of this patent is extended or adjusted under 35 U.S.C. 154(b) by 0 days.

(21) Appl. No.: 11/340,372

(22) Filed: Jan. 26, 2006

(65) Prior Publication Data
US 2007/0005070 A1    Jan. 4, 2007

Related U.S. Application Data

(60) Provisional application No. 60/691,170, filed on Jun. 16, 2005.

(51) Int. Cl.
*B25B 23/10* (2006.01)
*A61B 17/86* (2006.01)
(52) U.S. Cl. .......................................... 81/451; 606/73
(58) Field of Classification Search ............ 81/451, 81/460; 606/73
See application file for complete search history.

(56) References Cited

U.S. PATENT DOCUMENTS

| | | | | | |
|---|---|---|---|---|---|
| 2,268,515 | A | * | 12/1941 | Olson | ......................... 81/460 |
| 2,329,398 | A | * | 9/1943 | Duffy | ........................ 606/104 |
| 2,604,912 | A | * | 7/1952 | Walker | ........................ 81/451 |
| 2,800,936 | A | * | 7/1957 | West | ........................... 81/460 |
| 3,449,988 | A | * | 6/1969 | Gallo, Sr. | ................ 81/176.15 |
| 3,552,389 | A | | 1/1971 | Allgower et al. | |
| 3,554,193 | A | | 1/1971 | Konstantinou | |
| 3,753,454 | A | * | 8/1973 | Totsu | ........................... 81/448 |
| 3,888,144 | A | * | 6/1975 | Parsons | ...................... 81/436 |
| RE28,841 | E | | 6/1976 | Allgower et al. | |
| 4,219,015 | A | | 8/1980 | Steinemann | |
| 4,314,489 | A | * | 2/1982 | Arcangeli | ..................... 81/451 |

(Continued)

FOREIGN PATENT DOCUMENTS

DE          3434807           7/1984

(Continued)

*Primary Examiner*—David B Thomas
(74) *Attorney, Agent, or Firm*—Hudak, Shunk & Farine Co. LPA

(57) ABSTRACT

The present invention relates to an orthopedic screw and a corresponding screw driver wherein the screw has a torque driving head with a rounded side a spherical wall for multiaxial use, a self starting, self tapping insertion tip and a threaded portion including a cancellous thread. The threaded portion has a major diameter defined by a spiraling thread and a minor diameter. The head is joined to the threaded portion by an area of from about 2 to about 6 turns of the thread along the longitudinal axis in which the minor diameter tapers by an angle of from about 4° to about 12° and the major diameter of the screw remaining substantially the same. The screw includes a multilobe torque driving recess joined to a cylindrical recess that corresponds to a cylindrical post on the torque driver so as to form a press fit which acts to self-center the screw, to help avoid stripping of the screw/driver interface and to hold the screw in place on the torque driver prior to implantation.

7 Claims, 1 Drawing Sheet

U.S. PATENT DOCUMENTS

| | | | |
|---|---|---|---|
| 4,408,601 A | 10/1983 | Wenk | |
| RE31,628 E | 7/1984 | Allgower et al. | |
| 4,513,744 A | 4/1985 | Klaue | |
| 4,537,185 A | 8/1985 | Stednitz | |
| 4,590,825 A * | 5/1986 | Vaughn | 81/451 |
| 4,708,132 A | 11/1987 | Silvestrini | |
| 4,716,893 A | 1/1988 | Fischer et al. | |
| 4,760,843 A | 8/1988 | Fischer et al. | |
| 5,019,080 A | 5/1991 | Hemer | |
| 5,139,499 A * | 8/1992 | Small et al. | 606/73 |
| 5,169,400 A | 12/1992 | Muhling et al. | |
| 5,364,400 A | 11/1994 | Rego, Jr. et al. | |
| 5,403,136 A | 4/1995 | Mathys | |
| 5,423,819 A * | 6/1995 | Small et al. | 606/73 |
| 5,598,753 A * | 2/1997 | Lee | 81/460 |
| 5,660,091 A * | 8/1997 | Stone et al. | 81/460 |
| 5,709,687 A * | 1/1998 | Pennig | 606/73 |
| 5,797,914 A | 8/1998 | Leibinger | |
| 5,925,048 A | 7/1999 | Ahmad et al. | |
| 5,954,722 A | 9/1999 | Bono | |
| 6,001,101 A * | 12/1999 | Augagneur et al. | 606/73 |
| 6,017,177 A * | 1/2000 | Lanham | 411/410 |
| 6,235,033 B1 | 5/2001 | Brace et al. | |
| D449,692 S | 10/2001 | Michelson | |
| 6,306,140 B1 | 10/2001 | Siddiqui | |
| 6,322,562 B1 | 11/2001 | Wolter | |
| 6,328,746 B1 * | 12/2001 | Gambale | 606/104 |
| 6,355,043 B1 | 3/2002 | Adam | |
| 6,393,953 B1 * | 5/2002 | Totsu | 81/452 |
| 6,565,573 B1 | 5/2003 | Ferrante et al. | |
| 6,575,975 B2 | 6/2003 | Brace et al. | |
| 6,620,195 B2 | 9/2003 | Goble et al. | |
| 6,629,977 B1 | 10/2003 | Wolf | |
| 6,635,059 B2 | 10/2003 | Randall et al. | |
| 6,730,092 B2 | 5/2004 | Songer | |
| 6,733,502 B2 | 5/2004 | Altarac et al. | |
| 6,875,216 B2 | 4/2005 | Wolf | |
| 6,886,431 B1 * | 5/2005 | Petrsorich | 81/436 |
| 6,890,334 B2 | 5/2005 | Brace et al. | |
| 6,951,158 B1 * | 10/2005 | Edland | 81/460 |
| 6,989,014 B2 * | 1/2006 | Justin et al. | 606/73 |
| 7,037,309 B2 * | 5/2006 | Weil et al. | 606/73 |
| 2003/0028193 A1 | 2/2003 | Weil et al. | |
| 2003/0045881 A1 | 3/2003 | Barouk et al. | |
| 2003/0074002 A1 | 4/2003 | West, Jr. | |
| 2003/0125744 A1 | 7/2003 | Contiliano et al. | |
| 2003/0125749 A1 | 7/2003 | Yuan et al. | |
| 2003/0153919 A1 | 8/2003 | Harris | |
| 2003/0158555 A1 | 8/2003 | Sanders et al. | |
| 2003/0187447 A1 | 10/2003 | Ferrante et al. | |
| 2003/0199878 A1 | 10/2003 | Pohjonen et al. | |
| 2004/0006345 A1 | 1/2004 | Vlahos et al. | |
| 2004/0030336 A1 | 2/2004 | Khanna | |
| 2004/0068319 A1 | 4/2004 | Cordaro | |
| 2005/0085913 A1 | 4/2005 | Fraser et al. | |
| 2005/0096657 A1 | 5/2005 | Autericque et al. | |
| 2006/0173461 A1 * | 8/2006 | Kay et al. | 606/73 |
| 2006/0173462 A1 * | 8/2006 | Kay et al. | 606/73 |
| 2006/0200151 A1 * | 9/2006 | Ducharme et al. | 606/73 |

FOREIGN PATENT DOCUMENTS

| | | |
|---|---|---|
| DE | 3434807 | 12/1984 |
| DE | 3538238 | 9/1986 |
| DE | 3601865 | 1/1987 |
| EP | 0 172 130 | 2/1986 |
| EP | 0172130 | 2/1986 |
| EP | 0 299 160 | 1/1989 |
| EP | 0299160 | 1/1989 |
| GB | 2 132 487 | 7/1984 |

* cited by examiner

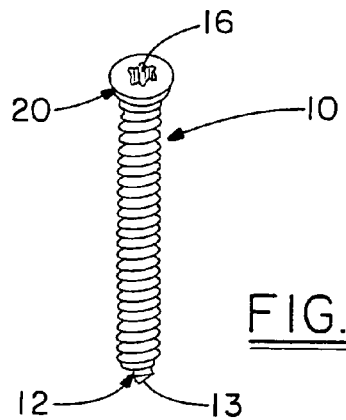
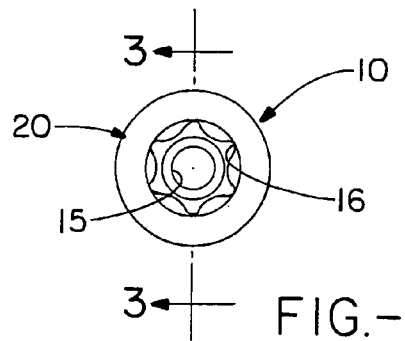
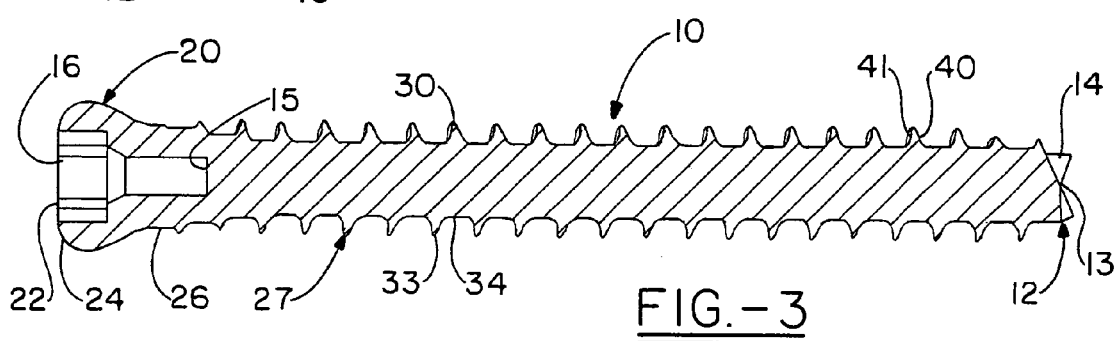
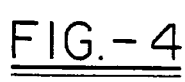
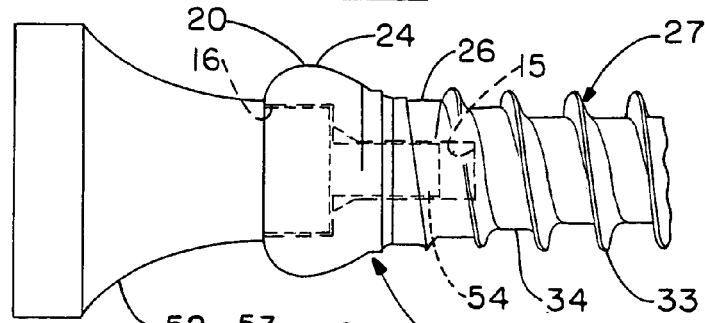
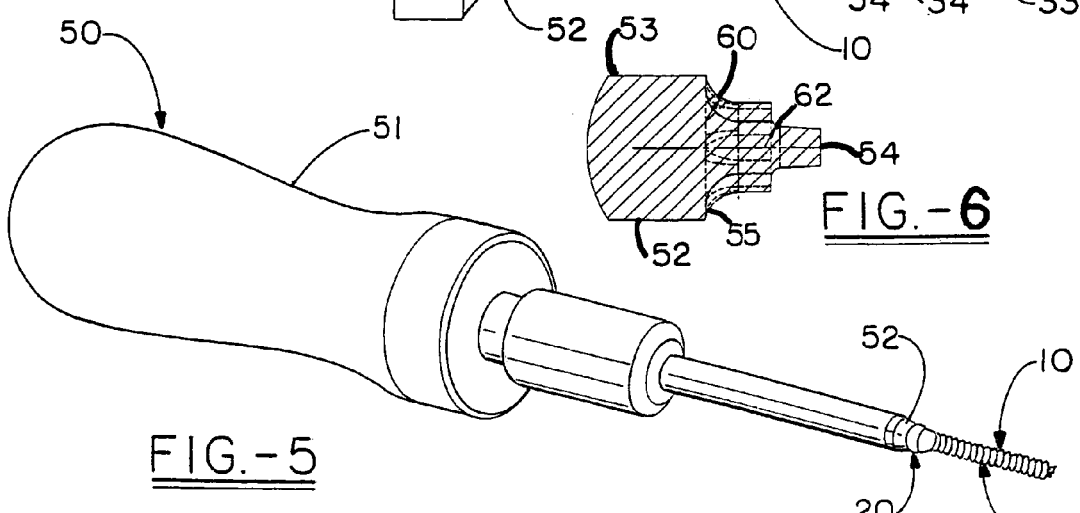

SELF-CENTERING SCREW AND RETAINING SCREW DRIVER FOR USE IN SURGERY

This application is based on U.S. Provisional Application Ser. No. 60/691,170, filed on Jun. 16, 2005

FIELD OF THE INVENTION

The present invention relates to a screw and screw driver which provides for a self-centering screw which is held in position on the driver for use in surgery, and in particular for use in orthopedic surgery.

BACKGROUND OF THE INVENTION

Increasing numbers of applications are being developed in the biomedical field, which involve the use of a mechanical construct that is surgically implanted to allow the body to mend or be reconstructed. These applications include spinal constructs and disk replacements, plates used for long bone repair from the femur to the metacarpals, and even soft tissue repair such as bladder and hernia repair. There are even orthopedic or dental areas in which a screw is implanted by itself to hold bone in a certain position, or to provide an anchor for a dental prosthetic.

One field which is ready for product growth is small bone surgery, i.e. below the elbow and ankle. Much of the work that has been done in this area in the past represents scaled down constructs and instruments from the large bone area. However, many of these products are not adequate for the fine bones and delicate procedures required of the small bone surgeon. These bones are fine and have minimal surface area for placement of an implant, and less mass for the placement of a screw. In addition, there is usually minimal soft tissue to cover an implant. These factors tend to make small bone surgery particularly tedious and unforgiving. Small bone surgeons are particularly appreciative of surgical tools that provide assistance in holding, centering, and implanting the delicate screws that are used in this area of the body, especially when it means that fewer hands need to be involved in the procedure.

The present invention is designed to meet the specific needs of the small bone surgeon to facilitate effective and repeatable procedures which provide for ease of use for this specific area of specialization, although it is certainly envisioned that the screw and screw driver of the present invention could be used in a wide variety of other orthopedic and surgical applications including spinal surgery, plating in various areas of the body, soft tissue repair, and bone anchoring.

The present invention provides a screw for use alone or as part of a construct which could include a plate. The screw is designed specifically for the small bone market, i.e. for use in bones distil to the elbow and knee, including, for example, the ulna, radius, tibia, fibula, as well as the metacarpals, carpals, metatarsals, tarsals, and phalanges. The screw can be used in applications previously mentioned, for example those that require fixation within a single bone such as the stabilization of a fracture or the screw can be used across two or more bones so as to facilitate total or partial fusion.

The screws are advantageously, self-starting, self-tapping screws having an internal torque driving recess that terminates in a cylindrical opening or cannulation. The cannulation can extend through the length of the screw or can extend only partially through the length of the screw in a partial cannula. The invention further includes a screw driver having an external torque driving shape and terminating in a conical or cylindrical pilot or boss which mates with the cylindrical cannula or tapered opening in the screw. The pilot is sized and held to a tolerance so as to hold the screw on the screw driver by a friction fit and further acts to center the screw's torque driving recess relative to the torque driver of the screw driver in order to help avoid stripping the torque driving recess of the driver. This is a particular problem for the small screws and even smaller torque driving recesses of the screws.

The screws include an insertion end having multiple flutes, and preferably 2 or 3 flutes about a conical recess. The screws further include a modified cancellous thread. The screw further has a partial taper of the minor diameter of about 5° to about 15°, and more preferably about 6° to about 10°, and most preferably about 8° over about the first 2 to about 6, and more preferably about 4 complete turns of the threads adjacent to the head of the screw.

The screws further include a torque driving recess that may be a hexagon, a sinusoidal shape, or a modification of a sinusoidal (multilobed) shape. This recess can be of a constant size in the direction of the longitudinal axis, or can taper inward along the longitudinal axis of the screw toward the bottom of the recess. The opening for the pilot of the screw driver can be of any cross section which corresponds to the cross-section of the pilot, but circular is preferable with a taper along the longitudinal axis in one of either the pilot or the hole. Thus, the pilot may have a slight taper and form an interference fit with a cylindrical opening, or alternatively and perhaps of slightly less advantage, the opening may have a slight taper and form an interference fit with a cylindrical pilot on the screw driver. A cylindrical opening with a slightly tapered, i.e. about 2-5°, pilot with a flat bottom works well, and is relatively easy to manufacture in the small sizes required. The driver and opening are dimensioned so that the distil end of the pilot is slightly smaller than the distil end of the opening, and the frictional fit optimally occurs right below a transition between the torque driving recess and the opening. An additional feature of the recess/opening is a chamfered transition area, which could be a truncated frutoconical shape that leads from the torque driving recess into the cylindrical opening. In addition, the head of the screw can include a rounded exterior portion or spherical shaped head to permit multiaxial insertion, i.e. in a corresponding rounded or spherical recess in a countersunk screw hole in a plate or other construct. The screws can be provided in typical lengths for small bone use, i.e. from about 5 mm to about 25 mm and typically in lengths of 8, 12 16 and 20 mm with a major diameter of about 2.7 mm or 3.5 mm. The screws can include a constant thread pitch as shown, in particular for use with a bone plate. A further embodiment of the screw for use in fixation by itself is a screw which includes a compression thread which increases in the number of turns over a given length. This variable pitch will preferably be used for the thread over about half of the distil end of the screw. The screws can be made of appropriate biocompatible material, including for example surgical grade stainless steel and titanium. The driver may be an integral design, such as stainless steel, or the pilot may be constructed as an insert for example from a more flexible material. Alternatively, the pilot may be constructed as a separate and preferably retractable assembly, such as a stylet, which rejects using the same mechanism as a retractable ball point pen. Preferably, the driver includes a fillet, or rounded transition between the shaft and the torque driving tip and also one between the torque driving tip and the pilot.

BRIEF DESCRIPTION OF THE DRAWINGS

FIG. 1 is a top perspective view of an orthopedic screw in accordance with the invention;

FIG. 2 is a top view of the screw shown in FIG. 1;

FIG. 3 is a cross-section of the screw taken along line 3-3 in FIG. 2;

FIG. 4 is a detail of a screwdriver and a screw head;

FIG. 5 is a side perspective view of a screw driver with a screw positioned on the driver; and FIG. 6 is a detail of a screwdriver head tip.

DETAILED DESCRIPTION OF THE INVENTION

FIGS. 1-3 show an orthopedic screw 10 in accordance with the present invention. The distal end of the screw includes a cutting tip 12 which is self-starting and self-tapping. The term "distal" is used herein to mean the end that would be farthest from the point of attachment to a plate if one were used, i.e. the insertion tip, and "proximal" is used to mean the opposite end of the screw, i.e. the head. The cutting tip 12 is provided by a conical recess 13 and a plurality of flutes 14 or grooves that form sharp cutting surfaces at the terminus of the screw. The invention could also be practiced with a blunt tip screw, such ad may be used for a cannulated version. The screw 10 includes a torque driving recess 16 terminating in a self-centering opening which can be a partial or full cannula 15 along its longitudinal axis. While the screw is shown as including a partial cannula in the drawings, the bore can extend fully toward the distal end of the screw, or can be absent. In a preferred embodiment the screw includes the partial cannulation which is a preferably a cylindrical or conical opening, and is more preferably a cylindrical recess extending at least about 1.5 mm up to about 5 mm, and preferably at least about 2 mm to 4 mm or more based upon the diameter of the screw. A chamfered or angled area 11 has a depth of about 0.05 to about 0.75 mm, or more preferably about 0.2 to about 0.4 mm and connects the cannulation or opening with the torque driving recess and further helps to guide the pilot of the screw driver into the opening 15. The opening is about 1.0 to about 2.0 mm, with a tolerance in the vicinity of about +/−0.001 to about +/−0.005 mm. If the opening is tapered, the pilot is preferably of a constant circular cross-section, so that the interference fit is created in the mating of the taper of either the opening or the pilot with the constant cross-section of its respective mate.

The cannulation is used with a torque driving instrument shown at 50 in FIG. 5 that has a torque driving head 52 which corresponds in shape to the female shape of the torque driving recess 16 of the screw and which terminates in a pilot, boss or post 54 that will fit in the centering opening 15 of the screw so that the screw is self-centering, is held in position on the torque driving instrument in a friction fit, and further which seats the screw so as to avoid stripping the interface between the screw and the torque driver. Preferably, the pilot has a circular cross-section which may vary in dimension along the longitudinal axis to cause the shape to taper from about 0.5 to about 10°, and preferably about 1 to about 5°, and most preferably about 2 to about 4°. The pilot has a length of about 1-5 mm, and preferably about 1-3 mm. The taper of the pilot causes a frictional fit between the pilot and the opening slightly below the chamfered area which holds the screw on the screw driver and helps to seat the torque driver in the torque driving recess. As is shown in the detail of the torque driving head in FIG. 6, the tip includes a first fillet 60 which forms a transition between the drive shaft 53 and the contoured tip 54, and a second fillet 62 which forms a transition between the contoured tip 54 and the pilot 54.

The head 20 of the screw includes a rounded area 21 which preferably includes from about 0.75 mm to about 2.0 mm of a sphere having a diameter of from about 4 mm to about 5 mm. This defines a side wall which will allow for multi-axial placement in a screw hole, for example, in a plate that has a corresponding concavity. In the event that the screw is used alone, the rounded area eliminates sharp transitions between the threaded area and the head of the screw.

The screw head 10 has a relatively flat proximal surface 22 having radiiused transitions 24 into the rounded area of the side wall of the head. The proximal surface includes a torque driving recess 16, such as a modified multilobe shape or torx shape as is shown in FIG. 2. The recess 16 can be of a constant cross-section or can taper toward the bottom. A necked area 26 joins the rounded area 21 of the head side wall to a threaded portion 27 of the screw. The threaded portion 27 includes a modified cancellous thread 30 with a constant major diameter 32 which is defined by the spiraling outer edge of the thread 33 and a minor diameter 34 defined by the inner portion of the screw at the base of the thread. The minor diameter 34 is constant over a distil portion of the thread so as to define a cylinder with a spiraling thread. The minor diameter also includes a proximal portion that tapers inward over the length of the first four proximal threads toward the distal end in order to improve fatigue strength and to improve compression at the proximal cortical bone interface and to compensate for bone re-adsorption. The tapered portion of the screw 36 includes a taper of from about 2° to about 20°, or more preferably from about 4° to about 12°, and most preferably about 6° to about 10° (i.e. about 8°) which tapers over from about 2 to about 10, and more preferably about 3 to about 6 complete turns (360°) of the thread 33. The pitch is between about 0.5 and 2.0 millimeters in length (i.e. a thread revolution of 360° per 0.5 to 2.0 millimeters).

The thread is a cancellous type thread with a front thrust 40 surface having an angle of from about 10° to about 30°, or more preferably from about 15° to about 25°, and most preferably about 18° to about 22° (i.e. about 20°) to a plane perpendicular to the longitudinal axis of the screw, while the rear surface 41 forms an angle of about 0° to about 10°, or more preferably from about 0° to about 8°, and most preferably about 3° to about 7° (i.e., about 5°) to the plane perpendicular to the longitudinal axis of the screw.

The screw can be made from an appropriate biocompatible material having appropriate strength characteristics including surgical grade stainless steel or titanium or absorptive materials. The driver can be made as an assembly where the torque driving head and shaft are made from biocompatible materials again having appropriate strength characteristics including surgical grade stainless steel or titanium. The pilot tip may be integral with the torque driving head, or may be a separate component made from the same or a different material, for example it could be a biocompatible ceramic, or plastic polymeric material which is press fit into a recess in the torque driving head. Alternatively, the pilot can be a retractable post which operates using the same mechanism that causes the retraction of a ball point pen, including a spring loaded button or a twist mechanism that advances the pilot or stylet.

FIG. 5 shows a screw driver 50 that is used with the screw of the invention. The screw driver includes a handle 51 that is preferably ergonometrically designed to feel comfortable in the hand of the surgeon and to provide an appropriate amount of torque per turn to avoid over torquing and stripping the screw. The shaft of the driver 50 terminates in a head that includes a torque driver 52 that includes pilot 54 to hold the screw in position on the screw driver by a friction fit as is shown in FIG. 4. This permits the surgeon to load the screw on the driver and than to manipulate the screw using the screw driver rather than to have to try to hold the screw between his or her fingers which would certainly obscure the view of the surgical cite. This greatly eases the surgeon's job and helps to relieve the possibility of cramping hands.

While in accordance with the patent statutes the best mode and preferred embodiment have been set forth, the scope of the invention is not limited thereto, but rather by the scope of the attached claims.

What is claimed is:

1. A surgical screw and screw driver, comprising:

a screw having a head and a insertion tip and a threaded portion with a longitudinal axis and having a major diameter defined by a spiraling thread and a minor diameter, the head having a terminal surface joined by a radiused area to a side wall further joined to the threaded portion, the terminal surface including a torque driving recess having a bottom wall with an opening along the longitudinal axis, the torque driving recess having a first cross sectional shape in the direction transverse to the longitudinal axis and the opening having a second cross sectional shape in the direction transverse to the longitudinal direction of the axis, the screw being made from surgical stainless steel or titanium; and a screw driver having a handle, a shaft and a torque driving head having a shape corresponding to the shape of the torque driving recess in the screw and terminating in a unitary pilot which has a frictional fit in the opening;

wherein the cross-sectional shape of the opening and of the pilot is circular in a direction transverse to the longitudinal axis and the cross-sectional shape of one of the opening and the pilot defines a dimension which is constant along the longitudinal axis and the other defines a dimension which continuously decreases along the longitudinal axis toward the bottom of the opening or the pilot.

2. A surgical screw as set forth in claim 1 wherein the shape of the torque driving recess is a hexagon, or a multilobe shape.

3. A surgical screw and screw driver, comprising:

a screw having a head and a insertion tip and a threaded portion with a longitudinal axis and having a major diameter defined by a spiraling thread and a minor diameter, the head having a torque driving recess having a bottom wall with an opening along the longitudinal axis, the torque driving recess having a multilobe or hexagonal cross sectional shape in the direction transverse to the longitudinal axis and the opening having a circular cross sectional shape in the direction transverse to the longitudinal direction of the axis, the screw being made from surgical stainless steel or titanium; and a screw driver having a handle, a shaft and a torque driving head having a first section which has a shape corresponding to the shape of the torque driving recess in the screw, a first filet forming a transition between the shaft and the first section, a second section having a pilot which has a circular cross-sectional shape and a second fillet which forms a transition between the first and second section, the pilot forming a frictional fit in the opening so as to hold the screw on the screw driver and the screw driver is self-centering in the screw so as to avoid stripping the torque driving recess in the screw.

4. A surgical screw as set forth in claim 3 wherein the dimension of one of the pilot and the opening tapers along the longitudinal axis.

5. An orthopedic screw as set forth in claim 3 wherein the thread is a has a front thrust surface having an angle of from about 10 to about 30 and a rear surface of from about 0 to about 10 to a plane perpendicular to the longitudinal axis of the screw and the minor diameter tapers over from about 2 to about 6 turns of the thread.

6. An orthopedic screw as set forth in claim 5 wherein the thread has a front thrust surface has an angle of from about 15 to about 25 and a rear surface of from about 0 to about 8 to a plane perpendicular to the longitudinal axis of the screw.

7. An orthopedic screw as set forth in claim 6 wherein the thread has a front thrust surface has an angle of from about 18 to about 22 and a rear surface of from about 3 to about 7 to a plane perpendicular to the longitudinal axis of the screw.

* * * * *